United States Patent [19]

Chandraratna

[11] Patent Number: 5,466,690
[45] Date of Patent: Nov. 14, 1995

[54] ACETYLENES DISUBSTITUTED WITH A HETEROAROMATIC GROUP AND A TETRALIN GROUP AND HAVING RETINOID LIKE ACTIVITY

[75] Inventor: Roshantha A. S. Chandraratna, Mission Viejo, Calif.

[73] Assignee: Allergan, Inc., Irvine, Calif.

[21] Appl. No.: 276,385

[22] Filed: Jul. 18, 1994

Related U.S. Application Data

[62] Division of Ser. No. 84,843, Jun. 29, 1993, Pat. No. 5,354,776, which is a division of Ser. No. 947,681, Sep. 21, 1992, Pat. No. 5,246,962, which is a division of Ser. No. 25,434, Mar. 13, 1987, Pat. No. 5,149,705.

[51] Int. Cl.⁶ .................. C07D 239/26; C07D 239/28; C07D 237/08; C07D 233/06; C07D 241/12; A61K 31/415

[52] U.S. Cl. .................. 514/247; 514/255; 514/269; 514/277; 514/354; 514/355; 514/356; 514/438; 514/448; 514/467; 514/471; 514/461; 544/224; 544/242; 544/335; 544/336; 544/386; 544/389; 544/398; 544/403

[58] Field of Search .................. 544/224, 242, 544/335, 336, 386, 389, 398, 403; 514/461, 471, 467, 356, 247, 255, 269, 277, 354, 355, 438, 448, 461

[56] References Cited

U.S. PATENT DOCUMENTS

| | | | |
|---|---|---|---|
| 3,870,726 | 3/1975 | Jager et al. | 548/314.7 X |
| 4,096,341 | 6/1978 | Frazer | 560/85 |
| 4,269,848 | 5/1981 | Bayssat et al. | 546/342 |
| 4,695,649 | 9/1987 | Magami et al. | 560/86 |
| 4,739,098 | 4/1988 | Chandraratna | 560/8 |
| 4,740,519 | 4/1988 | Shroot et al. | 514/443 |
| 4,810,804 | 3/1989 | Chandraratna | 514/311 |
| 4,826,969 | 5/1989 | Maignan et al. | 536/55.2 |
| 4,855,320 | 8/1989 | Chatterjee et al. | 514/473 |
| 4,895,868 | 1/1990 | Chandraratna | 514/432 |
| 4,980,369 | 12/1990 | Chandraratna | 514/432 |
| 4,992,468 | 2/1991 | Chandraratna | 514/532 |
| 5,006,530 | 4/1991 | Chandraratna | 514/546 |
| 5,013,744 | 5/1991 | Chandraratna | 514/456 |
| 5,015,658 | 5/1991 | Chandraratna | 514/345 |
| 5,023,341 | 6/1991 | Chandraratna | 514/432 |
| 5,045,551 | 9/1991 | Chandraratna | 514/337 |
| 5,053,523 | 10/1991 | Chandraratna | 514/337 |
| 5,068,053 | 11/1991 | Reiffenrath et al. | 252/299.61 |
| 5,068,252 | 11/1991 | Chandraratna | 514/398 |
| 5,089,509 | 2/1992 | Chandraratna | 514/337 |
| 5,090,992 | 2/1992 | Lawson | 71/92 |
| 5,100,909 | 3/1992 | Moon et al. | 514/397 |
| 5,132,307 | 7/1992 | Baumgarth et al. | 514/247 |
| 5,137,905 | 8/1992 | Moon et al. | 514/392 |
| 5,149,705 | 9/1992 | Chandraratna | 514/356 |
| 5,175,185 | 12/1992 | Chandraratna | 514/445 |
| 5,234,926 | 8/1993 | Chandraratna | 514/253 |
| 5,246,762 | 9/1993 | Chandraratna | 514/438 |
| 5,354,776 | 10/1994 | Chandraratna | 514/461 |

FOREIGN PATENT DOCUMENTS

| | | | |
|---|---|---|---|
| 0779885 | 3/1968 | Canada | 544/403 |
| 0111695 | 6/1984 | European Pat. Off. | 544/224 |
| 0130795 | 1/1985 | European Pat. Off. | 514/337 |
| 0176034 | 4/1986 | European Pat. Off. | 514/335 |
| 0284288 | 9/1986 | European Pat. Off. | 514/336 |
| 0224725 | 6/1987 | European Pat. Off. | 544/335 |
| 0350856 | 7/1989 | European Pat. Off. | 514/335 |
| 7803863 | 8/1979 | Finland | 546/342 |
| 8503626 | 3/1986 | Finland | 546/342 |
| 3708060 | 9/1987 | Germany | 514/335 |
| 3832570 | 3/1990 | Germany | 544/335 |
| 2208860 | 4/1989 | United Kingdom | 544/335 |
| 2263277 | 7/1993 | United Kingdom | 544/336 |

*Primary Examiner*—Floyd D. Higel
*Attorney, Agent, or Firm*—J. Mark Hoch; Robert J. Baran; Martin A. Voet

[57] ABSTRACT

Retinoid-like activity is exhibited by compounds of the formula

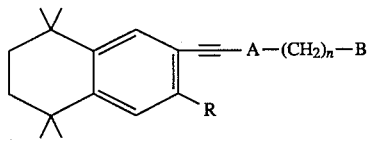

where R is hydrogen or lower alkyl; A is pyridyl, thienyl, furyl, pyridazinyl, pyrimidinyl or pyrazinyl; n is 0–5; and B is H, —COOH or an ester or amide thereof, —CH$_2$OH or an ether or ester derivative thereof, or —CHO or an acetal derivative thereof, or —COR$_1$ or a ketal derivative thereof where R$_1$ is —(CH$_2$)$_m$CH$_3$ where m is 0–4; or a pharmaceutically acceptable salt thereof.

6 Claims, No Drawings

ACETYLENES DISUBSTITUTED WITH A HETEROAROMATIC GROUP AND A TETRALIN GROUP AND HAVING RETINOID LIKE ACTIVITY

This patent application is a divisional patent application of U.S. Ser. No. 08/084,843, now U.S. Pat. No. 5,354,776, which was filed 29 Jun., 1993 in the name of Chandraratna which is a division of U.S. Ser. No. 07/947,681, now U.S. Pat. No. 5,246,962, which was filed on 21 Sep., 1992 in the name of Chandraratna which us itself a division of U.S. Ser. No. 07/025,434, now U.S. Pat. No. 5,149,705, which was filed on 13 Mar., 1987 in the name of Chandraratna.

BACKGROUND

This invention relates to novel compounds having retinoid-like activity. More specifically, the invention relates to compounds having an ethynylheteroaromatic acid portion and a second portion which is a tetrahydro naphthalene group. The acid function may also be converted to an alcohol, aldehyde or ketone or derivatives thereof, or may be alkyl or H.

RELATED ART

Carboxylic acid derivatives useful for inhibiting the degeneration of cartilage of the general formula 4-(2-(4,4-dimethyl-6-X)-2-methylvinyl)benzoic acid where X is tetrahydroquinolinyl, chromanyl or thiochromanyl are disclosed in European Patent Application 0133795 published Jan. 9, 1985. See also European Patent Application 176034A published Apr. 2, 1986 where tetrahydro naphthalene compounds having an ethynylbenzoic acid group are disclosed.

SUMMARY OF THE INVENTION

This invention covers compounds of formula I

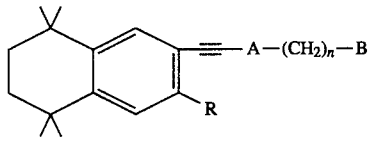

where R is hydrogen or lower alkyl; A is pyridyl, thienyl, furyl, pyridazinyl, pyrimidinyl or pyrazinyl; n is 0–5; and B is H, —COOH or a pharmaceutically acceptable salt, ester or amide thereof, —CH$_2$OH or an ether or ester derivative thereof, or —CHO or an acetal derivative thereof, or —COR$_1$ or a ketal derivative thereof where R$_1$ is —(CH$_2$)$_m$CH$_3$ where m is 0–4; or a pharmaceutically acceptable salt thereof.

In a second aspect, this invention relates to the use of the compounds of formula I for treating dermatoses, such as acne, Darier's disease, psoriasis, icthyosis, eczema, atopic dermatitis and epithelial cancers. These compounds are also useful in the treatment of arthritic diseases and other immunological disorders (e.g., lupus erythematosus), in promoting wound healing and in treating dry eye syndrome and in reversing the effects of sun damage to the skin.

This invention also relates to a pharmaceutical formulation comprising a compound of formula I in admixture with a pharmaceutically acceptable excipient, particularly one having anti-psoriatic activity. In another aspect, this invention relates to the process for making a compound of formula I which process comprises reacting a compound of formula II with a compound of formula III in the presence of Pd(PQ$_3$)$_4$ (Q is phenyl) or a similar complex

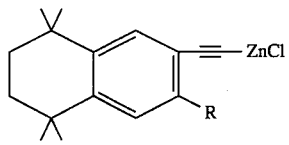

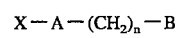

where X is a halogen, preferably I; n and A are defined above; and B is H, or a protected acid, alcohol, aldehyde or ketone, giving the corresponding compound of formula I; or converting an ester to an acid or salt; or converting an acid of formula I to a salt; or converting an acid of formula I to an ester; or converting an acid of formula I to an amide; or reducing an acid of formula I to an alcohol or aldehyde; or converting an alcohol of formula I to an ether or ester; or ozidizing an alcohol of formula I to an aldehyde; or converting an aldehyde of formula I to an acetal; or converting a ketone of formula I to a ketal; or converting an alcohol of formula I to a methyl group.

GENERAL EMBODIMENTS

Definitions

The term "ester" as used here refers to and covers any compound falling within the definition of that term as classically used in organic chemistry. Where B is —COOH, this term covers the products derived from treatment of this function with alcohols. Examples are the C$_1$ to C$_6$ alkyl esters or C$_1$ to C$_6$ alkylphenyl esters. Where the ester is derived from compounds where B is —CH$_2$OH, this term covers compounds of the formula —CH$_2$OOCR' where R' is any substituted or unsubstituted aliphatic, aromatic or aliphatic-aromatic group, particularly those of 7 to 10 carbons.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Here, and where ever else used, lower alkyl means having 1–6 carbon atoms. Also preferred are the phenyl or lower alkylphenyl esters.

Amide has the meaning classically accorded that term in organic chemistry. In this instance it includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals includes the radicals of the formula —CK where K is (—OR')$_2$. Here, R' is lower alkyl. Also, K may be —OR$_1$O— where R$_1$ is lower alkyl of 2–5 carbon atoms, straight chain or branched.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficeintly basic as to be capable of forming acid addition salts, such may be formed with any inorganic or organic acids or alkylating agent such a methyl iodide. Preferred acid addition salts are those formed with inorganic acids such as hydrochloric acid, sulfuric acid or phosphoric acid. Any of a number of simple organic acids having one, two or three carboxyl groups may be used for making acid addition salts.

The preferred compounds of this invention are those where the ethynyl group and the B group are attached to the 2 and 5 positions respectively of a pyridine ring (the 6 and 3 positions in the nicotinic acid nomenclature being equivalent to the 2/5 designation in the pyridine nomenclature) or the 5 and 2 positions respectively of a thiophene or furan group; n is 0, 1 or 2; and B is —COOH, an alkali metal salt or organic amine salt, or a lower alkyl ester thereof, or —CH$_2$OH and the lower alkyl esters and thereof. The more preferred compounds are:

ethyl 6-[2-(5,5,8,8-tetramethyl-5,6,7,8-tetrahydronaphth-2-yl)ethynyl]nicotinoate; and 6-[2-(5,5,8,8-tetramethyl-5,6,7,8-tetrahydronaphth-2-yl)ethynyl]nicotinic acid.

The compounds of this invention may be administered systemically or topically, depending on such considerations as the condition to be treated, need for site-specific treatment, quantity of drug to be. administered, and similar considerations.

In the treatment of dermatoses, it will generally be preferred to administer the drug topically, though in certain cases such as treatment of severe cystic acne, oral administration may also be used.

Any common topical formulation such as a solution, suspension, gel, ointment, or salve and the like may be used. Preparation of such topical formulations are well described in the art of pharmaceutical formulations as exemplified, for example, *Remington's Pharmaceutical Science*, Edition 17, Mack Publishing Company, Easton, Pa. For topical application, these compounds could also be administered as a powder or spray, particularly in aerosol form.

Other medicaments can be added to such topical formulation for such secondary purposes as treating skin dryness, providing protection against light; other medications for treating dermatoses, preventing infection, reducing irritation, inflammation and the like.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or for intermuscular injection.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a topical formulation containing between 0.01 and 0.5 milligrams per milliliter of formulation will constitute a therapeutically effective concentration. If administered systemically, an amount between 0.01 and 1 mg per kg body weight per day will effect a therapeutic or prophylatic result in most instances.

The retinoic acid-like activity of these compounds was confirmed through the classic measure of retinoic acid activity involving the effect of retinoic acid on ornithine decarboxylase. The original work on the correlation between retinoic acid and decrease in cell proliferation was done by Verma & Boutwell, *Cancer Research*, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-0-tetradecanoylphorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in *Cancer Res.*: 1662–1670, 1975.

SPECIFIC EMBODIMENTS

The compound of this invention can be made by a number of different synthetic chemical pathways. To illustrate this invention, there is here outlined a series of steps which have been proven to provide the compounds of formula I when such synthesis is followed in fact and in spirit. The synthetic chemist will readily appreciate that the conditions set out here are specific embodiments which can be generalized to any and all of the compounds represented by formula 1.

Compounds of formula I where the R group on the phenyl ring is hydrogen were prepared as follows:

Reaction Scheme I

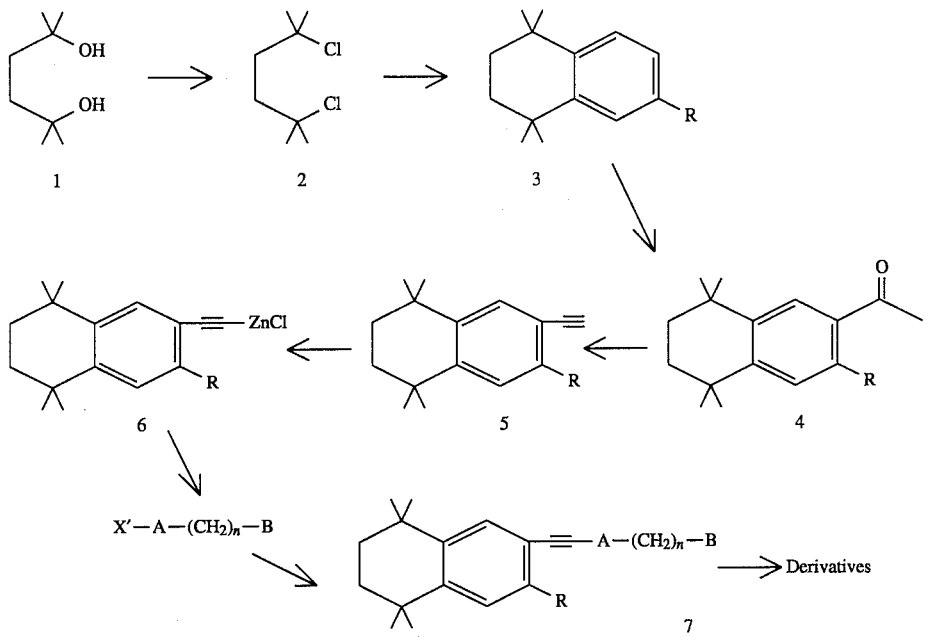

Here, n is 0–5 and B is H, or a protected acid, alcohol, aldehyde or ketone. X is Br, Cl or I but preferrably Br or I when n is 0. I is preferred when n is 1–5.

Compounds of formula I where R is methyl were prepared as per Reaction Scheme II.

talline precipitate is collected and repeatedly washed with water and then dried, for example, under vacuum.

Compound 3, the tetramethyltetrahydronaphthalene, is prepared by reacting the 2,5-dichloro-2,5-dimethylhexane compound with benzene under Freidel-Crafts conditions.

Reaction Scheme II

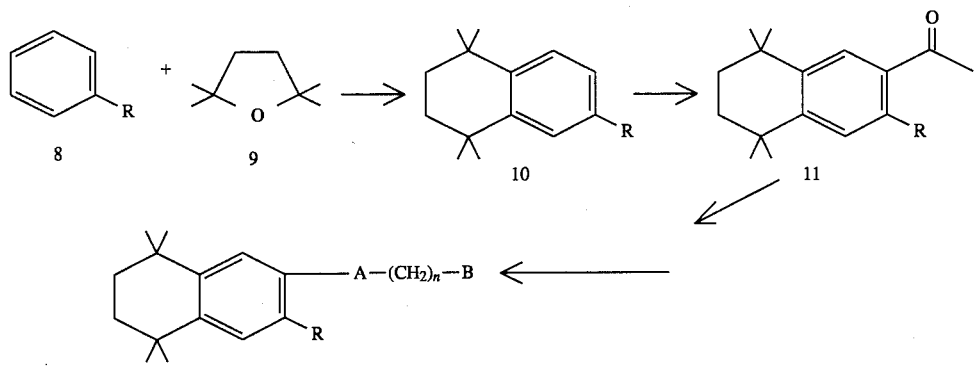

The definitions of R is lower alkyl, n, A, B and X are the same as in Scheme I.

A general description for making each of the compounds recited in the foregoing Reaction Schemes follows.

In Reaction Scheme I, The ethynyl tetrahydro naphthalene fragment is made as follows. The 2,5-dihydroxy-2,5-dimethylhexane of formula 1 is converted to its corresponding dichloride by treating the dihydroxy compound with hydrogen chloride gas. The reaction is effected at room temperature or thereabout by bubbling hydrogen chloride gas through an aqueous hydrochloric acid suspension of the dihydroxy compound until a saturated solution is obtained. The dichloride precipitates from the solution during the process of saturation with hydrogen chloride gas. The crys- For example, the 2,5-dichloro- material is dissolved in benzene which has been cooled to between about –10° and 10° C. Approximately a 50% molar excess of anhydrous aluminum chloride relative to the 2,5-dichloro- material is added. After addition of the anhydrous aluminum chloride, the mixture is stirred at between about 10° and 50° C., preferably at room temperature, for between 1 and 6 hours, preferably 3 hours. The solution is then refluxed for about 30 minutes to 2 hours, but preferably approximately 1 hour. The resulting solution is acidified and the product recovered by extraction and other means such as fractional distillation.

The ketone of formula 4 is obtained by treating the tetrahydronaphthalene with acetyl chloride in the presence of aluminum chloride. A suspension of the aluminum chloride in a polar inert solvent is prepared under an inert atmosphere and at reduced temperature, i.e., −10° to 10° C. The inert atmosphere may be argon or nitrogen, preferably argon. The reaction is conveniently carried out in a solvent such as methylene chloride. To the aluminum chloride suspension is added the tetrahydronaphthalene and acetyl chloride via a dropping funnel or similar device. About a 5% molar excess of acetyl chloride and 10% molar excess of aluminum chloride, relative to the tetrahydronaphthalene material, is used. The reaction is effected with agitation (stirring) over 0.5–4 hours at a temperature between 10°–50° C. Preferably the reaction is effected in about 2 hours at room temperature. Then the reaction is quenched with water and/or ice, the product extracted and further purified by distillation or some other appropriate means.

The acetelynic function of formula 5 is introduced by means of lithium diisopropylamide or a similar base at reduced temperature under an inert atmosphere. The reaction is carried out in an ether-type of solvent such as a dialkyl ether or a cyclic ether, for example, tetrahydrofuran, pyran or the like.

More specifically, lithium diisopropylamide is generated in situ by mixing diisopropylamine in a dry solvent such as tetrahydrofuran, which is then cooled, to between −70° and −50° C. under an inert atmosphere. An equimolar amount of an alkyllithium compound such as n-butyl lithium in an appropriate solvent is then added at the reduced temperature and mixed for an appropriate time to permit formation of lithium diisopropylamide (LDA). The ketone of formula 4 (at least a 10% molar excess) is dissolved in the reaction solvent, the solution cooled to that of the LDA mixture, and added to that solution. After brief mixing, the solution is then treated with a dialkyl chlorophosphate, preferably diethyl chlorophosphate in about a 20% molar excess. The reaction solution is then gradually brought to room temperature. This solution is then added to a second lithium diisopropylamide solution which is prepared in situ using dry solvent all under an inert atmosphere, preferrably argon, at reduced temperature (eg. −78° C.). Thereafter, the reaction mixture is again warmed to room temperature where it is stirred for an extended period of time, preferably between 10 and 20 hours, most preferably about 15 hours. The solution is then acidified and the product recovered by conventional means.

Formula 6 compounds are prepared under conditions which exclude water and oxygen. A dry, ether-type solvent such as dialkyl ether or a cyclic ether such as a furan or pyran, particularly a tetrahydrofuran, may be used as the solvent. A solution of formula 5 is first prepared under an inert atmosphere such as argon or nitrogen, and then a strong base such as n-butyl lithium is added (in about a 10% molar excess). This reaction is begun at a reduced temperature of between −10° and +10° C., preferably about 0° C. The reaction mixture is stirred for a short period, between 30 minutes and 2 hours, and then treated with about a 10% molar excess of fused zinc chloride dissolved in the reaction solvent. This mixture is stirred for an additional 1–3 hours at about the starting temperature, then the temperature is increased to about ambient temperature for 10–40 minutes.

Where a protected heteroaromatic compound is needed to couple with formula 6 compounds, such may be prepared from their corresponding acids, alcohols, ketones or aldehydes. These starting materials, the acids, alcohols aldehydes or ketones, are all available from chemical manufacturers or can be prepared by published methods. Acids are esterified by refluxing the acid in a solution of the appropriate alcohol in the presence of thionyl chloride or by reacting the acid and alcohol in the presence of dicyclohexylcarbodiimide and dimethyl aminopyridine. Alcohols, aldehydes and ketones all may be protected by forming, respectively, ethers and esters, acetals or ketals by known methods referenced below.

To increase the value of n before effecting a coupling reaction, where such compounds are not available from a commercial source, the heteraromatic compounds where B is —COOH are subjected to homologation by successive treatment under Arndt-Eistert conditions. These acids are then esterified by the general procedure outlined in the preceeding paragraph. To make formula 7, the heteroaromatic compound is dissolved in a dry reaction solvent. The heteroaromatic compound is used in an amount approximating the molar concentration of formula 6. This solution is introduced into a suspension of tetrakis-triphenylphosphine palladium (about a 5 to 10% molar amount relative to the reactants) in the reaction solvent at a temperature of between about −10° and +10° C. This mixture is stirred briefly, for about 15 minutes. To this just prepared mixture is then added the pre-prepared solution of formula 6, the addition being made at about room temperature. This solution is stirred for an extended period, between about 15 and 25 hours at room temperature. The reaction is then quenched with acid and the product separated and purified by conventional means to give the compounds of formula 7.

An alternate means for making compounds where n is 1–5 is to subject the compounds of formula 7 where B is an acid function to homologation using the Arndt-Eistert method referred to above.

The acids and salts derived from formula 7 are readily obtainable from the corresponding esters. Basic saponification with an alkali metal base will provide the acid. For example, an ester of Formula 7 may be dissolved in a polar solvent such as an alkanol, preferably under an inert atmosphere at room temperature, with about a three molar access of base, for example, potassium hydroxide. The solution is stirred for an extended period of time, between 15 and 20 hours, cooled, acidified and the hydrolysate recovered by conventional means.

The amide may be formed by any appropriate amidation means known in the art. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10° and +10° C. The last mentioned solution is then stirred at the reduced temperature for 1–4 hours, preferably 2 hours. Solvent removal provides a residue which is taken up in an inert inorganic solvent such as benzene, cooled to about 0° C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/ oxalyl chloride in methylene chloride (Omura, K., Swern, D. *Tetrahedron*, 1978, 34, 1651).

Ketones can be prepared from an appropriate aldehyde by treating the aldehyde with an alkyl Grignard reagent or similar reagent followed by oxidation using the reagents described above.

Acetals or ketals can be prepared from the corresponding aldehyde or ketone by the method described in March, Ibid, p 810.

Compounds where B is H are prepared from the corresponding halo-heterocyclic entity preferably where the halogen is I. This haloheterocyclic compound is reacted with the ethynyl zinc chloride entity as described in Reaction Scheme I and more specifically in Example 9. Halo-substituted heterocyclic compounds where B is H are commercially available or can be prepared by methods in the literature. Alternatively, compounds where n=1–5 and B is H, can be prepared by reducing the appropriate aldehyde or ketone using the Huang-Minlon modification of the Wolf-Kishner reduction or a similar reaction (March, ibid, pg. 1119).

Reaction Scheme II outlines a method for making compounds of Formula I where R is methyl. They are prepared under Freidel-Crafts conditions using 2,2,5,5-tetramethyltetrahydrofuran (formula 9) and toluene (formula 8). The furan, in a 3 to 4 molar excess, is added to toluene which has been cooled to between approximately −10° and 15° C. Anhydrous aluminum chloride is added in small portions with stirring in a molar amount approximating that of the toluene. When addition of the aluminum chloride is completed, the cooling bath is removed and the reaction allowed to proceed at room temperature for up to 20 hours. The solution is then refluxed for about 1 to 3 hours, preferably about 2 hours, after which the reaction is quenched by adding a dilute solution of hydrochloric acid, preferably about 3N in concentration. The reaction product is extracted from the aqueous layer and further purified by appropriate means, for example, fractional distillation.

Further synthetic steps to transform compound 10 in Reaction Scheme II to those of Formula I follows the steps and conditions outlined above under the discussion of Reaction Scheme I above.

The following Examples are set out to illustrate the the invention, not to limit its scope.

EXAMPLE 1

2,5-Dichloro-2,5-dimethylhexane

Hydrogen chloride gas was bubbled through a suspension of 48 g (0.33 mol) of 2,5-dimethyl-2,5-hexanediol in 600 ml conc. hydrogen chloride until the solution was saturated. The resulting crystalline product was collected by filtration, washed repeatedly with water and dried on a vacuum line to give the title compound as a crystalline white solid. PMR (CDCl$_3$): δ1.60 (12H, s), 1.94 (4H, s).

EXAMPLE 2

1,1,4,4-Tetramethyl-1,2,3,4-tetrahydronaphthalene

A vigorously stirred solution of 100 g (0.55 mol) of 2,5-dichloro-2,5-dimethylhexane in 300 ml benzene was cooled in an ice bath and treated with 45 g (0.34 mol) of anhydrous aluminum chloride in small portions. This mixture was stirred at room temperature for 3 hours, refluxed for 1 hour, cooled and poured into a mixture of ice and hydrogen chloride. The organic layer was recovered and the aqueous layer extracted with ether. Organic extracts were combined, washed with water, saturated Na$_2$CO$_3$ and saturated NaCl solutions and dried (MgSO$_4$).

After removing the solvent, the residue was fractionally distilled (78° C., 0.8 mm) to give the title compound as a colorless liquid. PMR (CDCl$_3$): δ1.3(12H, s), 1.7 (4H, s), 7.1 (2H,m), 7.5 (2H,m).

EXAMPLE 3

1,1,4,4-Tetramethyl-1,2,3,4-tetrahydro-6-acetylnaphthalene

A suspension of 3.45 g (25.9 mmol) aluminum chloride in 15 ml methylene chloride was cooled under argon in an ice/salt bath and treated while stirring with a mixture of 4 g (21.2 mmol) 1,1,4,4-tetramethyl-1,2,3,4-tetrahydro naphthalene (from Example 2) and 1.94 g (24.7 mmol) acetylchloride via a dropping funnel over a period of 0.5 hours. Then the cooling bath was removed, the mixture stirred for 2 hours at room temperature and the reaction quenched with ice. The organic layer was recovered and the aqueous layer extracted with 2×50 ml methylene chloride.

The organic extracts were combined and washed with water, saturated NaHCO$_3$ solution and dried (MgSO$_4$). solvent was removed in vacuo and the residue kugelrohr distilled (90° C.; 0.45 mm) to give the title compound as a colorless oil. PMR (CDCl$_3$): δ1.32(6H, s), 1.33 (6H, s,), 1.72(4H, s), 2.60(3H, s), 7.41(1H, d, J~8.8 Hz), 7.71(1H, dd, J~8.8, 2.6 Hz) 7.96 (1H, d, J~2.6 Hz)

EXAMPLE 4

1,1,4,4-Tetramethyl-6-ethynyl-1,2,3,4-tetrahydronaphthalene

To a stirred solution of 1.1572 g (11.4359 mmol) of diisopropylamine in 20 ml of dry tetrahydrofuran under argon at −78° C. was added dropwise via syringe, 7.2 ml of 1.6M (11.52 mmol) n-butyllithium in hexane. This mixture was stirred at −78° C. for 1 hour and then treated dropwise with a solution of 2.635 g (11.4391 mmol) of 1,1,4,4-tetramethyl-1,2,3,4-tetrahydro-6-acetylnaphthalene in 6 ml of dry tetrahydrofuran. After stirring at −78° C. for 1 hour, the mixture was treated with 1.97 g (11.4175 mmol) of diethyl chlorophosphate. The cooling bath was then removed and the mixture stirred at room temperature for 3.5 hours. This mixture was then transferred using a double ended needle to a solution of lithium diisopropylamide [prepared using 2.31 g (22.83 22 mmol) of diisopropylamine and 14.5 ml of 1.6M (23.2 mmol) n-butyllithium in hexane] in 60 ml of dry tetrahydrofuran at −78° C. Stirring was commenced at room temperature and continued for 20 hours. The reaction was then quenched with 50 ml water and acidified with 25 ml of 3N hydrogen chloride. Reaction product was recovered by extracting with 5×50 ml pentane. Organic extracts were combined and washed with 3N hydrogen chloride, water, saturated NaHCO$_3$ and saturated NaCl solutions and then dried (MgSO$_4$). Solvent was then removed and residue purified by flash chromatography (silica, 5% ethylacetate in hexane) followed by kugelrohr distillation (60° C., 0.2 mm) to give the title compound as a colorless oil. PMR (CDCl$_3$): δ1.25 (6H, s), 1.27(6H, S), 1.66 (4H, s), 2.98 (1H, S, 7.24 (2H, s), 7.46 (1H, s).

EXAMPLE 5

1,1,4,4,6-Pentamethyl-1,2,3,4-tetrahydronaphthalene

To a cooled (0° C.) mixture of 40 g (0.4341 mol) toluene and 25 g (0.195 mol) 2,2,5,5-tetramethyl tetrahydrofuran was added in small portions with stirring 26.6 g (0.2 mol) of anhydrous aluminum chloride. The cooling bath was removed and mixture stirred at room temperature for 20 hours and then heated at reflux for 2 hours. The reaction mixture was cooled to room temperature and then quenched by adding a mixture of ice and 100 ml 3N hydrogen chloride. The organic layer was separated and the aqueous layer extracted with 3×75 ml ether. Organic extracts were combined and washed with 3N hydrogen chloride, saturated $NaHCO_3$ and saturated NaCl solutions and dried ($MgSO_4$). Solvent was removed in vacuo and the residue fractionally distilled to give the title compound as a colorless oil. PMR ($CDCl_3$): 1.30 (6H, S), 1.32 (6H, S), 1.70 (4H, S), 2.33 (3H, S), 6.98 (1H, d, J~7 Hz), 7.14 (1H, S), 7.23 (1H, d, J~7 Hz).

Proceeding in a similar manner, but substuting for toluene the appropriate alkylphenyl moiety, there may be prepared the following compounds:
1,1,4,4-tetramethyl-6-ethyl-1,2,3,4-tetrahydronaphthalene;
1,1,4,4-tetramethyl-6-propyl-1,2,3,4-tetrahydronaphthalene;
1,1,4,4-tetramethyl-6-butyl-1,2,3,4-tetrahydronaphthalene; and
1,1,4,4-tetramethyl-6-pentyl-1,2,3,4-tetrahydronaphthalene.

EXAMPLE 6

1,1,4,4,7-Pentamethyl-6-acetyl-1,2,3,4-tetrahydronaphthalene

To a suspension of 13.72 g (102.9 mmol) aluminum chloride in 40 ml dichloroethane, which was cooled in an ice-acetone bath under argon, was added with stirring over a 1 hour period a solution of 17.11 g (84.56 mmol) of the 1,1,4,4,6-Pentamethyl-1,2,3,4-tetrahydronapthalene (from Example 5) in 10 ml dichloroethane. The cooling bath was removed and the mixture stirred at room temperature for 3 hours and then poured onto ice. The organic layer was separated and the aqueous layer extracted with 3×75 ml methylene chloride. The organic layers were combined and washed several times with water, then saturated $NaHCO_3$ and saturated NaCl solutions and then dried ($MgSO_4$). Solvent was removed in vacuo and the residue subjected to Kugelrohr distillation (70° C., 0.15 mm) to give the title compound as a low-melting yellow solid. PMR ($CDCl_3$): δ1.30 (6H, s), 1.32 (6H, s), 1.70 (4H, s), 2.51 (3H, s), 2.59 (3H, s), 7.16 (1H, s), 7.69 (1H, s)

Likewise, the compounds prepared as per Example 5 are converted to the corresponding acetyl form.

EXAMPLE 7

1,1,4,4,7-Pentamethyl-1,2,3,4-tetrahydronaphthalene

To a stirred solution of 794.2 mg (7.8486 mmol) diisopropylamine in 7 ml dry tetrahydrofuran under argon at −78° C. was added dropwise 4.9 ml of 1.6M (7.84 mmol) n-butyllithium in hexane. This solution was stirred at −78° C. for 1.25 hours and then treated via a double ended needle with a solution of 1.9 g (7.7749 mmol) of 1,1,4,4,7-pentamethyl-6-acetyl-1,2,3,4-tetrahydronapthalene in 4 ml dry tetrahydrofuran. After stirring at −78° C. for 1 hour, the mixture was treated with 1.3134 g (7.6117 mmol) of diethyl chlorophosphate. The cooling bath was removed and mixture stirred at room temperature for 3 hours. This material was then transferred using a double ended needle into a solution of lithium diisopropylamide [prepared as above using 1.5884 g (15.6972 mmol) of diisopropylamine and 10 ml of 1.6M (16 mmol) n-butyllithium in hexane] in 15 ml dry tetrahydrofuran at −78° C. The cooling bath was removed and mixture stirred at room temperature for 15 hours, then quenched with 50 ml water, and acidified to pH 1 with 3N hydrogen chloride. The mixture was extracted with 3×75 ml petroleum ether and the organic extracts were combined, washed with saturated $NaHCO_3$ and saturated NaCl solutions and dried ($MgSO_4$). Solvent was then removed in vacuo and the residue purified by flash chromatography (silica; 3% ethyl acetate in hexane) followed by kugelrohr distillation (50° C., 0.05 mm) to give the title compound as a colorless oil. PMR ($CDCl_3$): δ1.28 (12H, s), 1.67 (4H, s), 1.42 (3H, s), 3.20 (1H, s), 7.15 (1H, s), 7.44 (1H, s).

In a similar manner, the 6-position alkyl analogues from Example 6 are converted to their corresponding ethynyl derivative exemplified by the following compounds:
1,1,4,4-tetramethyl-6-ethyl-7-ethynyl-1,2,3,4-tetrahydronapthalene;
1,1,4,4-tetramethyl-6-propyl-7-ethynyl-1,2,3,4-tetrahydronaphthalene;
1,1,4,4-tetramethyl-6-butyl-7-ethynyl-1,2,3,4-tetrahydronaphthalene; and
1,1,4,4-tetramethyl-6-pentyl-7-ethynyl-1,2,3,4-tetrahydronaphthalene.

EXAMPLE 8

Ethyl 6-chloronicotinoate

A mixture of 15.75 g (0.1 mol) 6-chloronicotinic acid, 6.9 g (0.15 mol) ethanol, 22.7 g (0.11 mol) dicyclohexylcarbodiimide and 3.7 g (0.03 mol) dimethylaminopyridine in 200 ml methylene chloride was heated at reflux for 2 hours. The mixture was allowed to cool, solvent removed in vacuo and residue subjected to flash chromatography to give the title compound as a low-melting white solid. PMR ($CDCl_3$): δ1.44 (3H, t, J~6.2 Hz) 4.44 (2H, q, J~6.2 Hz), 7.44 (1H, d, J~8.1 Hz), 8.27 (1H, dd, J~8.1 Hz, 3 Hz), 9.02 (1H, d, J3 Hz).

This procedure may be used to esterify any of the other halo-substituted acids employed in the making of these compounds such as
ethyl-2-(2-chloropyrid-5-yl)acetate;
ethyl-5-(2-chloropyrid-5-yl)pentanoate;
ethyl-2-(2-iodofur-5-yl)acetate;
ethyl-5-(2-iodofur-5-yl)pentanoate;
ethyl-2-(2-iodothien-5-yl)acetate;
ethyl-5-(2-iodothien-5-yl)pentanoate;
ethyl-5-(3-chloropyridazin-6-yl)acetate; and
ethyl-5-(3-chloropyridazin-6-yl)pentanoate.

EXAMPLE 9

Ethyl 6-[2-(5,5,8,8-tetramethyl-5,6,7,8-tetrahydronaphth-2-yl)ethynyl]nicotinoate The reaction vessels used in this procedure were flame dried under vacuum and all operations were carried out in an oxygen-free argon or nitrogen atmosphere. To a solution of 417.6 mg (1.9667 mmol) of 1,1,4,4-tetramethyl-1,2,3,4-tetrahydro-6-ethynylnapthalene in 3 ml of dry tetrahydrofuron (THF) at 0° C. was added dropwise 1.3 ml of 1.6M (2.32 mmol) n-butyllithium in hexane. This mixture was stirred at 0° C. for 10 minutes and at room temperature for 15 minutes, cooled again to 0° C. and then treated by double-ended needle with a solution of 290 mg (2.1279 mmol) of fused zinc chloride in 4 ml dry THF. The mixture was stirred at 0° C. for 45 minutes and at room temperature for 15 minutes. A solution of 361.1 mg (1.9455 mmol) of ethyl 6-chloronicotinoate in 4 ml dry THF was transferred by double ended needle into a suspension of 420 mg (0.3635 mmol) of tetrakistriphenylphosphine palladium in 4 ml dry THF, the resultant mixture stirred at room temperature for 15 minutes and then treated by double ended needle with the solution of alkynyl zinc prepared above. The reaction mixture was stirred at room temperature for 70 hours and then quenched with ice and 30 ml of 3N HCl. The resultant mixture was extracted with 3×50 ml of ether, the ether extracts combined and washed successively with saturated $NaHCO_3$ and saturated NaCl solutions and then dried ($MgSO_4$). The ether solution was filtered and concentrated in-vacuo. The resultant crude product was purified by flash chromatography (silica, 10% ethyl acetate in hexanes) followed by recrystallization from a mixture of ethylacetate in hexane to give the title compound as a pale cream solid.

PMR ($CDCl_3$): δ1.28 (6H, s), 1.30 (6H, s), 1.43 (3H, t, J~7.1 Hz), 1.69 (4H, s), 4.42 (2H, q, J~7.1 Hz), 7.31 (1H, d, J~8.3 Hz), 7.38 (1H, d, J~8.3 Hz), 7.59 (1H, d, J~8.3 Hz), 7.60 (1H, s), 8.28 (1H, dd, J~8.3 Hz, 2.5 Hz), 9.20 (1H, d, J~2.5 Hz).

Proceeding in a similar manner, but substituting 1,1,4,4, 6-pentamethyl-6-ethynyl-1,2,3,4-tetrahydronaphthalene from Example 7 or another compound prepared as per that Example for the 1,1,4,4-tetramethyl compound of the preceding paragraph and, if appropriate, a suitable halogen-substituted heterocycle for ethyl 6-chloronicotinoate, there can be prepared the following compounds:

ethyl 6-[2-(3,5,5,8,8-pentamethyl-5,6,7,8-tetrahydronaphth-2-yl)ethynyl]nicotinoate;
ethyl 6-[2-(3-ethyl-5,5,8,8-tetramethyl-5,6,7,8-tetrahydronaphth- 2-yl)ethynyl]nicotinoate;
ethyl 6-[2-(3-pentyl-5,5,8,8-tetramethyl-5,6,7,8-tetrahydronaphth- 2-yl)ethynyl]nicotinoate;
ethyl [2((5,5,8,8-tetramethyl-5,6,7,8-tetrahydronaphth-2-yl)ethynyl)pyrid-5-yl]acetate;
ethyl 3-[2-((5,5,8,8-tetramethyl-5,6,7,8-tetrahydronaphth-2-yl)ethynyl)pyrid-5-yl]propionate;
ethyl 5-[2-((5,5,8,8-tetramethyl-5,6,7,8-tetrahydronaphth-2-yl)ethynyl)pyrid-5-yl]pentanoate;
ethyl [5-((5,5,8,8-tetramethyl-5,6,7,8-tetrahydronaphth-2-yl)ethynyl)fur-2-yl]acetate;
ethyl 3-[5-((5,5,8,8-tetramethyl-5,6,7,8-tetrahydronaphth-2-yl)ethynyl)fur-2-yl]propionate;
ethyl 5-[5-((5,5,8,8-tetramethyl-5,6,7,8-tetrahydronaphth-2-yl)ethynyl)fur-2-yl]pentanoate;
ethyl [5-((5,5,8,8-tetramethyl-5,6,7,8-tetrahydronaphth-2-yl)ethynyl)thien-2-yl]acetate;
ethyl 3-[5-((5,5,8,8-tetramethyl-5,6,7,8-tetrahydronaphth-2-yl)ethynyl)thien-2-yl]propionate;
ethyl 5-[5-((5,5,8,8-tetramethyl-5,6,7,8-tetrahydronaphth-2-yl)ethynyl)thien-2-yl]pentanoate;
ethyl [6-((5,5,8,8-tetramethyl-5,6,7,8-tetrahydronaphth-2-yl)ethynyl)pyridazin-3-yl]acetate;
ethyl 3-[6-((5,5,8,8-tetramethyl-5,6,7,8-tetrahydronaphth-2-yl)ethynyl)pyridazin-3-yl]propionate;
ethyl 5-[6-((5,5,8,8-tetramethyl-5,6,7,8-tetrahydronaphth-2-yl)ethynyl)pyridazin-3-yl]pentanoate;
ethyl [5-((5,5,8,8-tetramethyl-5,6,7,8-tetrahydronaphth-2-yl)ethynyl)pyrimidin-2-yl]acetate;
ethyl 3-[5-((5,5,8,8-tetramethyl-5,6,7,8-tetrahydronaphth-2-yl)ethynyl)pyrimidin-2-yl]propionate;
ethyl 5-[5-((5,5,8,8-tetramethyl-5,6,7,8-tetrahydronaphth-2-yl)ethynyl)pyrimidin-2-yl]pentanoate;
ethyl [2-((5,5,8 ,8-tetramethyl-5,6,7,8-tetrahydronaphth-2-yl)ethynyl)pyrimidin-5-yl]acetate;
ethyl 3-[2-((5,5,8,8-tetramethyl-5,6,7,8-tetrahydronaphth-2-yl)ethynyl)pyrimidin-5-yl]propionate;
ethyl 5-[2-((5,5,8,8-tetramethyl-5,6,7,8-tetrahydronaphth-2-yl)ethynyl)pyrimidin-5-yl]pentanoate;
ethyl [5-((5,5,8 ,8-tetramethyl-5,6,7,8-tetrahydronaphth-2-yl)ethynyl)pyrazin-2-yl]acetate;
ethyl 3-[5-((5,5,8,8-tetramethyl-5,6,7,8-tetrahydronaphth-2-yl)ethynyl)pyrazin-2-yl]propionate; and
ethyl 5-[5-((5,5,8,8-tetramethyl-5,6,7,8-tetrahydronaphth-2-yl)ethynyl)pyrazin-2-yl]pentanoate.

EXAMPLE 10

6-[2-(5,5,8,8-tetramethyl-5,6,7,8-tetrahydronaphth-2-yl)ethynyl]nicotinic acid

Absolute ethanol was degassed by applying a vacuum while simultaneously bubbling nitrogen through it. A solution of 188 mg (0.5201 mmol) ethyl 6-[2-(5,5,8,8-tetramethyl- 5,6,7,8-tetrahydronaphth-2-yl)ethynyl]nicotinoate in 2 ml absolute ethanol was treated with 800 ml of a 1.65M (1.32 mmol) solution of potassium hydroxide in ethanol and water. The mixture was stirred at room temperature for 18 hours and then the solvent removed in vacuo. The residue was dissolved in water and extracted with 50 ml ether, which was discarded. The aqueous layer was then acidified with glacial acetic acid and extracted with 4×50 ml ether. The ether extracts were combined, washed with water, saturated NaCl solution and then dried ($MgSO_4$). Solvent was removed in vacuo to give the title compound as a pale yellow solid. PMR ($CDCl_3$): δ1.31 (12H, s), 1.71(4H, s), 7.34 (1H, d, J~7.8 Hz), 7.40 (1H, d, J~7.8 Hz), 7.62 (1H, s), 8.39 (1H, dd, J~7.3 Hz, 2.1 Hz), 9.33 (1H, d, J~2.1 Hz).

In the same manner, any of the esters prepared in Example 9 may be converted to their corresponding acid.

EXAMPLE 11

2-[2-(5,5,8,8-tetramethyl-5,6,7,8-tetrahydronaphth-2-yl)ethynyl]-5-hydroxymethylpyridine A 250 ml 3-necked flask is fitted with a stirrer, a dropping funnel, a nitrogen inlet and a thermometer. In the flask is placed a solution of 379.5 mg (10 mmol) of lithium aluminum hydride in 30 ml of dry diethyl ether. The solution is cooled to −65° C. under nitrogen and a solution of 3.6148 g (10 mmol) of ethyl 6-[2-(5,5,8,8-tetramethyl- 5,6,7,8-tetrahydronaphth-2-yl)ethynyl]nicotinoate in 15 ml of dry ether is added dropwise at a rate such that the temperature does not exceed −60° C. The mixture is stirred at −30° C. for 1 hour and the excess hydride is then destroyed by the addition of 300 mg (3.4 mmol) of ethyl acetate. The reaction mixture is then hydrolyzed by adding 3 ml of saturated ammonium chloride solution and allowing the temperature to rise to room temperature. The mixture is then filtered and the residue washed with ether. The ether layer is then washed with saturated sodium chloride solution, dried ($MgSO_4$) and then concentrated in vacuo. The residue is purified by chromatography followed by recrystalliztion to give the title compound.

EXAMPLE 12

2-[2-(5,5,8,8-tetramethyl-5,6,7,8-tetrahydronaphth-2-yl) ethynyl]-5-acetoxymethylpyridine A solution of 3.195 g (10 mmol) of 2-[2-(5,5,8,8-tetramethyl- 5,6,7,8-tetrahydronaphth-2-yl)ethynyl]-5-hydroxymethylpyridine, 600 mg (10 mmol) of glacial acetic acid, 2.06 g (10 mmol) of dicyclohexylcarbodiimide and 460 mg (3.765 mmol) of 4-dimethylaminopyridine in 150 ml methylene chloride is stirred at room temperature for 48 hours. The reaction mixture is then filtered and the residue washed with 50 ml of methylene chloride. The filtrate is then concentrated in vacuo and the residue is purified by chromatography followed by recrystallation to give the title compound.

By the same process, any acid or ester of this invention may be converted to its corresponding primary alcohol analog.

EXAMPLE 13

2-[2-(5,5,8,8-tetramethyl-5,6,7,8-tetrahydronaphth-2-yl)ethynyl]-pyridine-5-carboxaldehyde A solution of 1.396 g (11 mmol) of freshly distilled oxalyl chloride in 25 ml of methylene chloride is placed in a 4-necked flask equipped with a stirrer, a thermometer and two pressure-equalizing addition funnels fitted with drying tubes. The solution is cooled to −60° C. and then treated dropwise with a solution of 1.875 g (24 mmol) of dimethyl sulfoxide (distilled from calcium hydride) in 5 ml of methylene chloride over a five minute period. The reaction mixture is then stirred at −60° C. for an additional 10 minutes. A solution of 3.195 g (10 mmol) of 2-[2-(5,5,8,8-tetramethyl-5,6,7,8-tetrahydronaphth-2-yl)ethynyl]-5-hydroxymethylpyridine in 10 ml of methylene chloride is then added to the reaction mixture over a period of 5 minutes. The mixture is stirred for a further 15 minutes and is then treated with 5.06 g (50 mmol) of triethylamine. The cooling bath is then removed and the mixture is allowed to warm to room temperature. Thirty ml of water is then added to the mixture and stirring is continued for a further 10 mintues. The organic layer is then separated and the aqueous layer is extracted with 20 ml of methylene chloride. The organic layers are then combined and washed successively with dilute HCl, water and dilute $Na_2CO_3$ solution and then dried ($MgSO_4$). The solution is then filtered and concentrated in vacuo and the residue is purified by chromatography followed by recrystallization to give the title compound.

All alcohols of this invention may be oxidized to their corresponding aldehyde by this method.

EXAMPLE 14

2-[2-(5,5,8,8-tetramethyl-5,6,7,8-tetrahydronaphth-2-yl)ethynyl]-5-(1-hydroxypropyl)pyridine Four ml of a 3M (12 mmol) solution of ethylmagnesium bromide in ether is placed in a 3-necked flask fitted with a mechanical stirrer, a reflux condenser protected by a drying tube and a pressure-equalizing dropping funnel protected by a drying tube. The flask is cooled in an ice-bath and a solution of 3.174 g (10 mmol) of 2-[2-(5,5,8,8-tetramethyl-5,6,7,8-tetrahydronaphth-2-yl)ethynyl] pyridine-5-carboxaldehyde in 10 ml of dry ether is added slowly with vigorous stirring. The cooling bath is then removed and the mixture heated at reflux for 3 hours. The mixture is then cooled in an ice-salt bath and 5 ml of saturated ammonium chloride solution is added. The mixture is stirred for a further 1 hour and then filtered and the residue washed with two 10 ml portions of ether. The ether solution is then separated, dried ($MgSO_4$) and the ether removed in vacuo. The residue is then purified by chromatography followed by recrystallization to give the title compound.

Using the same procedure, but substituting for the pyridine compound noted above, any of the other heteroaromatic aldehydes of this invention can be converted to a secondary alcohol.

Such secondary alcohols may be converted to their corresponding ketone using the same reagents in approximately the same relative amounts of reagent to reactant and essentially the same conditions described in Example 13.

EXAMPLE 15

2-[2-(5,5,8,8-tetramethyl-5,6,7,8-tetrahydronaphth-2-yl)ethynyl]-5-dimethoxymethylpyridine A round-bottomed flask is fitted with a Dean-Stark apparatus under a reflux condenser protected by a drying tube. A mixture of 3.174 g (12 mmol) of 2-[2-(5,5,8,8-tetramethyl-5,6,7,8-tetrahydronaphth-2-yl)ethynyl]pyridine- 5-carboxaldehyde, 4.80 mg (15 mmol) of anhydrous methanol, 2 mg of p-toluenesulfonic acid monohydrate and 10 ml of anhydrous benzene is placed in the flask and the mixture heated at reflux under nitrogen until close to the theoretical amount of water is collected in the Dean-Stark trap. The reaction mixture is cooled to room temperature and washed successively with 5 ml of 10% sodium hydroxide solution and two 5 ml portions of water and then dried ($MgSO_4$). The solution is then filtered and the solvent removed in vacuo. The residue is purified by chromatography and then recrystalliztion to give the title compound.

In a similar manner, any aldehyde or ketone of any compound of this invention may be converted to an acetal or a ketal.

EXAMPLE 16

Preferably, these compounds may be administered topically using various formulations. Such formulation may be as follows.

| Ingredient | Weight/Percent |
| --- | --- |
| Solution | |
| Retinoid | 0.1 |
| BHT | 0.1 |
| Alcohol USP | 58.0 |
| Polyethylene Glycol 400 NF | 41.8 |
| Gel | |
| Retinoid | 0.1 |
| BHT | 0.1 |
| Alcohol USP | 97.8 |
| Hydroxypropyl Cellulose | 2.0 |

What is claimed is:

1. A compound of the formula

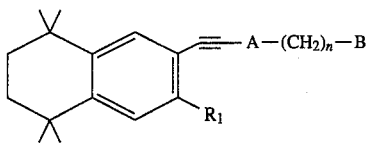

where R is hydrogen or lower alkyl; A is pyridazinyl, pyrimidinyl, or pyrazinyl; n is 0–5; and B is H, —COOH or a pharmaceutically acceptable salt, or ester of saturated aliphatic alcohols of ten or fewer carbon atoms, or the cyclic or saturated aliphatic cyclic alcohols of 5 to 10 carbon atoms, or phenol, or amide or mono- or disubstituted amide of saturated aliphatic amines of 10 or fewer carbon atoms, or the cyclic or saturated aliphatic cyclic radicals of 5 to 10 carbon atoms thereof, —CH$_2$OH or a lower alkyl ether or ester of saturated aliphatic acids of ten or fewer carbon atoms or the cyclic or saturated aliphatic cyclic acids of 5 to 10 carbon atoms, or benzoic acid thereof, or —CHO or a lower alkyl acetal derivative thereof, or —COR$_1$ or a lower alkyl ketal derivative thereof where R$_1$ is (CH$_2$)$_m$CH$_3$ where m is 0–4; or a pharmaceutically acceptable salt thereof.

2. The compound of claim 1 where R is hydrogen or methyl, n is 0, 1 or 2.

3. The compound of claim 2 where B is —COOH or a pharmaceutically acceptable salt, ester or amide thereof.

4. A pharmaceutical composition comprising a pharmaceutically acceptable excipient and a compound of the formula

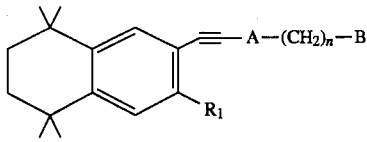

where R is hydrogen or lower alkyl; A is pyridazinyl, pyrimidinyl, or pyrazinyl; n is 0–5; and B is H, —COOH or a pharmaceutically acceptable salt, or ester of saturated aliphatic alcohols of ten or fewer carbon atoms, or the cyclic or saturated aliphatic cyclic alcohols of 5 to 10 carbon atoms, or phenol, or amide or mono- or disubstituted amide of saturated aliphatic amines of 10 or fewer carbon atoms, or the cyclic or saturated aliphatic cyclic radicals of 5 to 10 carbon atoms thereof, —CH$_2$OH or a lower alkyl ether or ester of saturated aliphatic acids of ten or fewer carbon atoms or the cyclic or saturated aliphatic cyclic acids of 5 to 10 carbon atoms or benzoic acid thereof, or —CHO or a lower alkyl acetal derivative thereof, or —COR$_1$ or a lower alkyl ketal derivative thereof where R$_1$ is (CH$_2$)$_m$CH$_3$ where m is 0–4; or a pharmaceutically acceptable salt thereof.

5. A composition according to claim 4 having anti-psoriatic activity in a mammal.

6. A method of treating psoriasis in a mammal which method comprises administering alone or in conjunction with a pharmaceutically acceptable excipient, a therapeutically effective amount of a compound of the formula

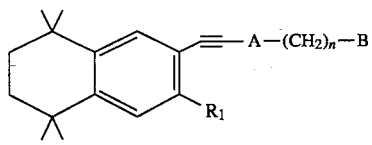

where R is hydrogen or lower alkyl; A is pyridazinyl, pyrimidinyl, or pyrazinyl; n is 0–5; and B is H, —COOH or a pharmaceutically acceptable salt, or ester of saturated aliphatic alcohols of ten or fewer carbon atoms, or the cyclic or saturated aliphatic cyclic alcohols of 5 to 10 carbon atoms, or phenol, or amide or mono- or disubstituted amide of saturated aliphatic amines of 10 or fewer carbon atoms, or the cyclic or saturated aliphatic cyclic radicals of 5 to 10 carbon atoms thereof, —CH$_2$OH or a lower alkyl ether or ester of saturated aliphatic acids of ten or fewer carbon atoms or the cyclic or saturated aliphatic cyclic acids of 5 to 10 carbon atoms, or benzoic acid thereof, or —CHO or a lower alkyl acetal derivative thereof, or —COR$_1$ or a lower alkyl ketal derivative thereof where R$_1$ is (CH$_2$)$_m$CH$_3$ where m is 0–4; or a pharmaceutically acceptable salt thereof.

* * * * *